(12) United States Patent
Zalipsky

(10) Patent No.: US 7,476,725 B2
(45) Date of Patent: Jan. 13, 2009

(54) PREPARATION OF MACROMOLECULAR CONJUGATES BY FOUR-COMPONENT CONDENSATION REACTION

(75) Inventor: Samuel Zalipsky, Redwood City, CA (US)

(73) Assignee: Alza Corporation, Mountain View, CA (US)

( * ) Notice: Subject to any disclaimer, the term of this patent is extended or adjusted under 35 U.S.C. 154(b) by 441 days.

(21) Appl. No.: 11/148,122

(22) Filed: Jun. 8, 2005

(65) Prior Publication Data

US 2005/0287113 A1 Dec. 29, 2005

Related U.S. Application Data

(60) Provisional application No. 60/578,199, filed on Jun. 8, 2004.

(51) Int. Cl.
*C07K 2/00* (2006.01)
(52) U.S. Cl. .................................................... 530/402
(58) Field of Classification Search ....................... None
See application file for complete search history.

(56) References Cited

U.S. PATENT DOCUMENTS

| | | | |
|---|---|---|---|
| 4,179,337 A | 12/1979 | Davis et al. | |
| 4,766,106 A | 8/1988 | Katre et al. | |
| 4,902,502 A | 2/1990 | Nitecki et al. | |
| 4,917,888 A | 4/1990 | Katre et al. | |
| 5,103,556 A | 4/1992 | Filip et al. | |
| 5,286,637 A * | 2/1994 | Veronese et al. | 435/183 |
| 5,395,619 A | 3/1995 | Zalipsky et al. | |
| 5,631,018 A | 5/1997 | Zalipsky et al. | |
| 5,932,462 A | 8/1999 | Harris et al. | |
| 6,048,720 A * | 4/2000 | Dalborg et al. | 435/219 |
| 6,077,939 A | 6/2000 | Wei et al. | |
| 6,274,554 B1 * | 8/2001 | Magal et al. | 514/12 |
| 6,600,525 B1 | 7/2003 | Sawai et al. | |

FOREIGN PATENT DOCUMENTS

| | | |
|---|---|---|
| DE | 101 50 077 A1 | 4/2003 |
| EP | 0 400 472 | 12/1990 |
| EP | 0 832 898 | 4/1998 |
| WO | WO 90/13540 | 11/1990 |
| WO | WO 92/16555 | 10/1992 |
| WO | WO 98/51697 | 11/1998 |
| WO | WO 01/37983 | 5/2001 |
| WO | WO 03/051795 | 7/2003 |
| WO | WO 2004/108634 | 12/2004 |

OTHER PUBLICATIONS

L.H. Brinkerhoff et al. Int. J. Cancer (1999) 83, pp. 326-334.*
Shearwater Corp. "Catalog 2001. Polyethylene Glycol and Derivatives for Biomedical Applications." (2001), 19 pages.*
H.F. Gaertner and R.E. Offord. Bioconj. Chem. (1996) 7(1), pp. 38-44.*
Y. Inada, et al. Methods Enzymol. (1994) 242, pp. 65-90.*
Chamow et al., *Bioconjugate Chem.* 5:133-140 (1994).
Davis et al., *J. Org. Chem.* 63:9614-9615 (1998).
de Nouy, A.E.J. et al., *Biomacromolecules* 1:259-267 (2000).
Dixon, H.B., *J. Protein Chem.* 3:99-108 (1984).
Domling, A. and Ugi, I., *Angew. Chem. Int. Ed.* 39:3168-3210 (2000).
Gaerthner, H.F. et al., *Bioconjugate Chem.* 3:262-6 (1992).
Geoghegan, K.F. et al., *Bioconjugate Chem.* 3:138-46 (1992).
Goldstein, L. et al., *Appl. Biochem. & Biotech.* 42:19-35 (1993).
Harris et al., *J. Polym. Sci. Polym. Chem. Ed.* 22:341-352 (1984).
King, T.P. et al., *Biochemistry* 25:5774-5779 (1986).
Llanos and Sefton, *Macromolecules* 24:6065-6072 (1991).
Marcaurelle, L.A. et al., *Org. Lett.* 3:3691-94 (2001).
Morehead, H.W. and Talmadge, K.W., *J. Chromat.* 587:171-176 (1991).
Monfardini, C. et al., *Bioconjugate Chem.* 6:62-9 (1995).
Obrecht D. et al., *Helvetica Chimica ACTA*, 80:65-72 (1997).
O'Shannessy, D.J. and Quarles, R.H., *J. Immunol. Methods* 99(2):153-61 (1987).
Park, W.K.C. et al., *J. Am. Chem. Soc.* 118:10150-10155 (1996).
Pollak and G.M. Whitesides, *J. Amer. Chem. Soc.* 98:289-291 (1976).
Rozzell, *Meth. Enzymol.* 136:479-497 (1987).
Ugi, I. et al., *Angew. Chemie* 71:386 (Abstract) (1959).
Veronese et al., (*Applied Biochem. and Biotech*, 11:141-152 (1985).
Vretblad, P. et al., *Acta Chemica Scandinavica* 27:2769-2780 (1973).
Wachter, E. and Werhahn, R. in Solid Phase Methods in Protein Sequence Analysis, Previero, A. & Coletti-Previero, M.-A., eds., Elsevier, pp. 185-192 (1977).
Weber and R. Staddler, *Polymer* 29:1064-1070 (1988).
Wilchek, M. and Bayer, E.A., *Methods of Enzymol.* 138:429-42 (1987).
Yarema, K.J. et al., *J. Biol. Chem.* 273:31168-79 (1998).
Zalipsky, S., *Adv. Drug Del. Rev.* 16:157-182 (1995).
Zalipsky, S., *Bioconj. Chem.* 6:150-165 (1995).
Zalipsky, S. et al., *Bioconjugate Chem.* 6:705-8 (1995).
Zalipsky, S. and Harris, J.M., Poly(EthyleneGlycol): Chemistry and Biological Applications, ACS Symp. Ser. 680, Washington, D.C. (1997).
Zalipsky, S. and Menon-Rudolph, S., in Poly(EthyleneGlycol): Chemistry and Biological Applications, Zalipsky, S. & Harris, J.M., eds., ACS Symp. Ser. 680, Washington, D.C. (1997), chapter 21, pp. 328-341.
Zalipsky et al., *J. Macromol. Sci. Chem.* A21:839-845 (1984).

* cited by examiner

*Primary Examiner*—Andrew D Kosar

(57) ABSTRACT

Polymer-biomolecule conjugates are prepared, generally in a site-specific or -selective manner, by a four-component condensation reaction. The method may be used to prepare conjugates having two polymer molecules attached at a single site on a biomolecule. The conjugates are typically water soluble and have beneficial pharmacological properties, such as reduced immunogenicity and increased circulation time.

6 Claims, 2 Drawing Sheets

PREPARATION OF MACROMOLECULAR CONJUGATES BY FOUR-COMPONENT CONDENSATION REACTION

This patent application claims priority to U.S. Provisional Application No. 60/578,199, filed on Jun. 8, 2004, which is incorporated herein in its entirety by reference.

FIELD OF THE INVENTION

The invention pertains to preparation of conjugates of biomolecules with water soluble polymers, and in particular to preparation of such conjugates by a four-component condensation reaction.

REFERENCES de Nouy, A. E. J. et al., *Biomacromolecules* 1:259-267 (2000).
Dixon, H. B., *J Protein Chem.* 3:99-108 (1984).
Domling, A. and Ugi, I., *Angew. Chem. Int. Ed.* 39:3168-3210 (2000).
Gaertner, H. F. et al., *Bioconjugate Chem.* 3:262-6 (1992)
Geoghegan, K. F. et al., *Bioconjugate Chem.* 3:138-46 (1992)
Goldstein, L. et al., *Appl. Biochem. &Biotech.* 42:19-35 (1993).
King, T. P. et al., *Biochemistry* 25:5774 (1986).
Marcaurelle, L. A. et al., *Org. Lett.* 3:3691-94 (2001)
Morehead, H. W. and Talmadge, K. W., *J. Chromat.* 587: 171-176 (1991)
Monfardini, C. et al., *Bioconjugate Chem.* 6:62-9 (1995)
O'Shannessy, D. J. and Quarles, R. H., *J. Immunol. Methods* 99(2): 153-61 (1987).
Page, P., PCT Pubn. No. WO 01/37983 (2001).
Park, W. K. C. et al., *J. Am. Chem. Soc.* 118:10150-10155 (1996).
Rodriguez, E. C. et al., *J. Org. Chem.* 63:9614 (1998).
Ugi, I. et al., *Angew. Chemie* 71:386 (1959).
Vretblad, P. et al., *Acta Chemica Scandinavica* 27:2769-2780 (1973).
Wilchek, M. and Bayer, E. A., *Methods of Enzymol.* 138: 429-42 (1987)
Wachter, E. and Werhahn, R. in SOLID PHASE METHODS IN PROTEIN SEQUENCE ANALYSIS, Previero, A. & Coletti-Previero, M.-A., eds., Elsevier (1977), pp. 185-192.
Yarema, K. J. et al., *J. Biol. Chem.* 273:31168-79 (1998).
Zalipsky, S., *Adv. Drug Del. Rev.* 16:157-182 (1995a).
Zalipsky, S., *Bioconj. Chem.* 6:150-165 (1995b).
Zalipsky, S. et al., *Bioconjugate Chem.* 6:705-8 (1995c)
Zalipsky, S. and Harris, J. M., POLY(ETHYLENEGLYCOL): CHEMISTRY AND BIOLOGICAL APPLICATIONS, ACS Symp. Ser. 680, Washington, D.C. (1997)
Zalipsky, S. and Menon-Rudolph, S., in POLY(ETHYLENEGLYCOL): CHEMISTRY AND BIOLOGICAL APPLICATIONS, Zalipsky, S. & Harris, J. M., eds., ACS Symp. Ser. 680, Washington, D.C. (1997), chapter 21, pp. 328-341.

BACKGROUND OF THE INVENTION

Hydrophilic polymers, such as polyethylene glycol (PEG), have been used for modification of various substrates, such as polypeptides, drugs and liposomes, in order to reduce immunogenicity of the substrate and/or to improve its blood circulation lifetime (Zalipsky & Harris, 1997). For example, parenterally administered proteins can be immunogenic and may have a short pharmacological half-life. Some proteins can also be relatively water insoluble. Consequently, it can be difficult to achieve therapeutically useful blood levels of the proteins in patients.

Conjugation of hydrophilic polymers, particularly PEG (Zalipsky & Harris, 1997), to proteins has been described as an approach to overcoming these difficulties. For example, Davis et al., in U.S. Pat. No. 4,179,337, describe the conjugation of PEG to proteins such as enzymes and insulin to form PEG-protein conjugates having less immunogenicity yet retaining a substantial proportion of physiological activity. Veronese et al. (*Applied Biochem. and Biotech,* 11: 141-152 (1985)) describe activating polyethylene glycols with phenyl chloroformates for conjugation to a ribonuclease and a superoxide dismutase, respectively. Katre et al., in U.S. Pat. Nos. 4,766,106 and 4,917,888, describe solubilizing proteins by polymer conjugation. U.S. Pat. No. 4,902,502 (Nitecki et al.) and PCT Pubn. No. WO 90/13540 (Enzon, Inc.) describe conjugation of PEG and other polymers to recombinant proteins to reduce immunogenicity and increase half-life.

PEG has also been described for use in improving the blood circulation lifetime of liposomes (U.S. Pat. No. 5,103,556). The PEG polymer is covalently attached to the polar head group of a lipid in order to mask or shield the liposomes from being recognized and removed by the reticuloendothelial system.

Various conjugation chemistries for attachment of PEG to biologically relevant molecules have been reviewed (Zalipsky, 1995a).

SUMMARY OF THE INVENTION

The invention provides a versatile method for preparing conjugates of water soluble polymers, preferably PEG polymers, with biologically active or biologically relevant molecules, particularly polypeptides. Conjugation to the biomolecule can often be carried out in a site specific or site selective manner. The method allows, for example, attachment of a PEG chain at a functional group on a polypeptide selected from an amine, a carboxylic acid, or a synthetically introduced aldehyde or ketone. The method also provides for preparation of diverse conjugates in a combinatorial fashion, if desired.

In one aspect, the invention provides a method of preparing a conjugate of a protein or polypeptide with a water soluble polymer, the method comprising:

reacting components (a)-(d) below:
(a) $R_A$—C(O)R' (a carbonyl component), where R' is H or lower alkyl, preferably H or methyl, and more preferably H (i.e. an aldehyde),
(b) $R_N$—$NH_2$ (an amine component),
(c) $R_C$—C(O)OH (a carboxylic acid component), and
(d) $R_I$—NC (an isonitrile component), to form a conjugated product incorporating at least one of each moiety represented by $R_A$, $R_N$, $R_C$, and $R_I$. At least one of (a)-(c) is said protein or polypeptide; that is, the reaction includes a protein or polypeptide bearing a reactive carbonyl ($R_A$—C(O)R'), a protein or polypeptide bearing a reactive amine ($R_N$—$NH_2$), and/or a protein or polypeptide bearing a reactive carboxylic acid ($R_C$—C(O)OH). At least one of (a)-(d) is a water soluble polymer; that is, the reaction includes a water soluble polymer bearing a reactive carbonyl ($R_A$—C(O)R'), water soluble polymer bearing a reactive amine ($R_N$—$NH_2$), water soluble polymer bearing a reactive carboxylic acid ($R_C$—C(O)OH), and/or water soluble polymer bearing a reactive isonitrile ($R_I$—NC).

In one embodiment, the conjugated product is of the form $R_I$NH—C(O)—CR'$R_A$—NR$_N$—C(O)R$_C$, incorporating exactly one residue of each of components (a)-(d). In other embodiments, e.g. in which one of the components (a)-(d) bears more than one of the reactive functionalities indicated (such as a component R$_N$—NH$_2$ bearing multiple amino groups, or a component R$_C$—C(O)OH bearing multiple carboxylic acid groups), the conjugate product may include said component conjugated to additional residues of the other components.

The polymer, and the conjugate formed therefrom, are preferably water soluble at room temperature at physiological pH.

The protein or polypeptide is represented by at least one component selected from (a)-(c) above, the water soluble polymer is represented by at least one different component selected from (a)-(d) above, and any remaining components of (a)-(d) are stable, non-interfering compounds, as defined herein. In a preferred embodiment, the protein or polypeptide is a single component selected from (a)-(c), the polymer is a different component selected from (a)-(d), and the remaining components of (a)-(d) are stable, non-interfering compounds.

The remaining components may selected from, for example, targeting moieties, labeling moieties, and benign (i.e. stable, non-interfering) "placeholder" groups. Preferably, the remaining components are low molecular weight compounds as defined herein. Such low molecular weight compounds preferably include those in which the group $R_A$, $R_N$, $R_C$ or $R_I$ (which may be represented by $R_X$) is a stable organic moiety having 1-12, preferably 1-8, carbon atoms and 0-4 heteroatoms selected from oxygen, nitrogen, and sulfur. The group $R_A$, $R_N$, or $R_C$ may also be hydrogen.

Preferably, $R_X$, when not hydrogen or methyl, includes linkages selected from alkyl, alkenyl, ether, hydroxyl, carboxylic ester, ketone, and amide. Non-limiting examples include lower alkyl groups, cycloalkyl groups, lower hydroxyalkyl groups, lower alkyl esters, and lower alkyl amides.

In selected embodiments, the protein or polypeptide is selected from (b) R$_N$—NH$_2$ and (c) R$_C$—C(O)OH. In further selected embodiments, the water soluble polymer is selected from (a) R$_A$—C(O)R', (b) R$_N$—NH$_2$, and (d) R$_I$—NC, or from (a) R$_A$—C(O)R', (b) R$_N$—NH$_2$, and (c) R$_C$—COOH. In still further embodiments, the polymer is selected from (a) R$_A$—C(O)R' and (b) R$_N$—NH$_2$. In the above embodiments, R' is preferably H. In another preferred embodiment, component (d), R$_I$—NC, is a water soluble polymer.

The water soluble polymer is preferably a functionalized polyalkylene oxide (PAO), such as polypropylene oxide (PPO) or, in a preferred embodiment, polyethylene glycol (PEG). Such a functionalized polyalkylene oxide molecule has an available carbonyl, amine, carboxyl, or isonitrile functionality (depending on whether the polymer is R$_A$—C(O)R', R$_N$—NH$_2$, R$_C$—COOH, or R$_I$—NC, respectively).

A PEG or PPO molecule having an isonitrile functionality, suitable for use in the conjugation methods described herein, itself forms another aspect of the invention. Such a molecule typically has the structure $R_{CAP}$(OCHR"CH$_2$)$_n$—X—N≡C, where R" is H or methyl, $R_{CAP}$ is a stable end capping group, X represents a direct bond or a stable linking moiety, and n is an integer between 10 and about 2300, such that, for example, the moiety —(OCH$_2$CH$_2$)$_n$—, when R" is H, has a molecular weight between about 440 and 100,000 Daltons. Exemplary molecular weights for the moiety —(OCH$_2$CH$_2$)$_n$— include, for example, 2000, 5000, 10,000, 20,000, and 40,000 Daltons.

In selected embodiments, $R_{CAP}$ is acyl, aryl or alkyl, e.g. methyl. The linker X preferably consists of linkages selected from alkyl, aryl, cycloalkyl, ether, amide, and combinations thereof. More preferably, X consists of linkages selected from alkyl, cycloalkyl, aryl and combinations of alkyl and aryl or alkyl and cycloalkyl. The linker is preferably up to about twelve atoms in length.

In one embodiment, each of components (a)-(d) is a single compound. In other embodiments, useful in combinatorial synthesis of conjugates, at least one of components (a)-(d) comprises a plurality of compounds.

Preferably, the conjugate of the protein or polypeptide with the water soluble polymer has reduced immunogenicity and/or an increased half life in circulation, when administered in vivo to a subject, including a human subject, compared to the unconjugated protein or polypeptide.

The conjugation reaction may include a variety of different combinations of the above-referenced components. Examples include the following subsets of reactions, in which the water soluble polymer component is exemplified by PEG. However, other water soluble polymers, e.g. PPO, may also be used in any of these reactions.

In a first subset of reactions, (c) is a protein, one of (a), (b) and (d) is a PEG reagent, and the remaining components are stable, non-interfering compounds. In these reactions, when (d) is a PEG-isonitrile reagent or (a) is a PEG-carbonyl reagent, component (b) is preferably a low molecular weight amine, which may be supplied in excess. When (b) is a PEG-amine reagent, the reagent is preferably a low pKa amine, e.g. a PEG oxyamine, a PEG hydrazide, a PEG carbazide, or a PEG aromatic amine.

In a related subset of reactions, useful for conjugating two polymer chains to a single attachment site on a protein molecule, (c) is a protein, two of (a), (b) and (d) are PEG reagents, and the remaining component is a stable, non-interfering compound.

In a second subset of reactions, (a) is a protein modified to contain an aldehyde or ketone group, one of (b), (c) and (d) is a PEG reagent, and the remaining components are stable, non-interfering compounds. In these reactions, when (b) is a PEG-amine reagent, the reagent is preferably a low pKa amine, e.g. a PEG hydrazide, a PEG carbazide, or a PEG aromatic amine, and (c) is preferably a low molecular weight carboxylic acid provided in excess, e.g. an acetate as a buffer component or additive. When (c) is a PEG-carboxyl reagent, (b) is preferably a low molecular weight amine provided in excess.

In a related subset of reactions, useful for conjugating two polymer chains to a single site on a protein molecule, (a) is a protein modified to contain a reactive carbonyl, e.g. aldehyde group, two of (b), (c) and (d) are PEG reagents, and the remaining component is a stable, non-interfering compound. In this case, when (b) is a PEG-amine reagent and (d) is a PEG-isonitrile reagent, a PEG-amine reagent, the amine reagent is preferably a low pKa amine, e.g. a PEG hydrazide, a PEG carbazide, or a PEG aromatic amine, and (c) is preferably a low molecular weight carboxylic acid provided in excess, e.g. acetate.

In third subset of reactions, (b) is a protein, one of (a), (c) and (d) is a PEG reagent, and the remaining two of (a), (c) and (d) are stable, non-interfering compounds. In these reactions, when (d) is a PEG-isonitrile reagent, (c) is preferably a low molecular weight carboxylic acid provided in excess.

In a related subset of reactions, useful for conjugating two polymers to a protein molecule, (b) is a protein, two of (a), (c) and (d) are PEG reagents, and the remaining component is a stable, non-interfering compound. In these reactions, when (a) is a PEG-carbonyl reagent and (d) is a PEG-isonitrile reagent, (c) is preferably a low molecular weight carboxylic acid provided in excess.

In another aspect, the invention provides a method of preparing a pharmaceutical composition, the composition comprising, in a pharmaceutical vehicle, a conjugate of a biologically active or relevant molecule with a biocompatible, preferably water soluble polymer, the method comprising:

(i) reacting components (a)-(d) below:
(a) $R_A$—C(O)R', where R' is H or lower alkyl, preferably H or Me, and most preferably H;
(b) $R_N$—$NH_2$,
(c) $R_C$—C(O)OH, and
(d) $R_I$—NC, to form a conjugated product incorporating at least one of each moiety represented by $R_A$, $R_N$, $R_C$, and $R_I$. In one embodiment, as discussed above, the conjugate is of the form $R_I$NH—C(O)—C$R_A$R'—N$R_N$—C(O)$R_C$, incorporating exactly one of each moiety represented by $R_A$, $R_N$, $R_C$, and $R_I$. In other embodiments, e.g. in which one of the components (a)-(d) bears more than one of the reactive functionalities indicated (such as a component $R_N$—$NH_2$ bearing multiple amino groups, or a component $R_C$—C(O)OH bearing multiple carboxylic acid groups), the conjugate product may include said component conjugated to multiple residues of the other components. See, for example, the hyaluronic acid conjugate of Example 16, below.

At least one of the components (a)-(d) is a biologically active or relevant molecule, and at least one of the components (a)-(d) is a biocompatible, preferably water soluble polymer; and (ii) formulating the conjugate, or a pharmaceutically acceptable salt thereof, in a pharmaceutical vehicle, preferably an aqueous vehicle. The conjugate formed is preferably water soluble at room temperature and physiological pH.

In forming the conjugate $R_I$NH—C(O)—C$R_A$R'—N$R_N$—C(O)$R_C$, the biologically active molecule is represented by at least one component selected from (a)-(d) above, and preferably selected from (a)-(c); the polymer is represented by at least one different component selected from (a)-(d) above; and any remaining components of (a)-(d) are selected from labeling moieties, targeting moieties, and other stable, non-interfering compounds. In a preferred embodiment, the molecule is one component selected from (a)-(c), the polymer is a different component selected from (a)-(d), and the remaining components of (a)-(d) are selected from labeling moieties, targeting moieties, and other stable, non-interfering compounds. Typically, the remaining components are low molecular weight compounds, as defined herein.

In preferred embodiments, the biologically active molecule is selected from (a) $R_A$—C(O)R', (b) $R_N$—$NH_2$, and (c) $R_C$—C(O)OH, and more preferably from (b) $R_N$—$NH_2$ and (c) $R_C$—C(O)OH. In selected embodiments, the molecule is a protein or polypeptide.

In further selected embodiments, the polymer is selected from (a) $R_A$—C(O)R', (b) $R_N$—$NH_2$, and (d) $R_I$—NC, or from (a) $R_A$—C(O)R', (b) $R_N$—$NH_2$, and (c) $R_C$—COOH. In still further embodiments, the polymer is selected from (a) $R_A$—C(O)R' and (b) $R_N$—$NH_2$. The polymer is preferably a functionalized polyalkylene oxide (PAO) such as polypropylene oxide (PPO) or, preferably, polyethylene glycol (PEG), e.g. a PEG molecule having an available carbonyl, amine or isonitrile functionality. In one particular embodiment, the polymer is a PEG isonitrile as disclosed herein.

The conjugation reaction of step (i) may include a variety of different combinations of the above-referenced components, including the first through third and related subsets of reactions described above. The protein in these reactions may be replaced with another biologically active molecule, such as a polysaccharide, polynucleotide, or small molecule drug compound.

Preferably, the conjugate of the biologically active molecule with the polymer has reduced immunogenicity, reduced degradation, and/or an increased half life in circulation, when administered in vivo to a subject, including a human subject, compared to the unconjugated biologically active molecule.

In a further aspect, the invention provides a water soluble conjugate of the form

wherein
at least one of $R_A$, $R_N$, and $R_C$ is a protein or polypeptide,
at least one of $R_I$, $R_A$, $R_N$, and $R_C$, preferably $R_I$, is a polyalkylene oxide, preferably polyethylene glycol (PEG); and
remaining members of $R_I$, $R_A$, $R_N$, and $R_C$ are independently selected from labeling moieties, targeting moieties, and R, where R is a stable organic moiety having 1-12, preferably 1-8, carbon atoms and 0-4 heteroatoms selected from oxygen, nitrogen, and sulfur. When R is an embodiment of $R_A$, $R_N$, or $R_C$, R may also be hydrogen. R' is preferably H or lower alkyl, e.g. $CH_3$, and is more preferably H.

Preferably, R, when not hydrogen or methyl, includes linkages selected from alkyl, alkenyl, ether, hydroxyl, carboxylic ester, ketone, and amide. Examples include lower alkyl groups, cycloalkyl groups, lower hydroxyalkyl groups, lower alkyl esters, and lower alkyl amides.

The conjugate is preferably water soluble at room temperature and physiological pH.

In the water soluble conjugate $R_I$NH—C(O)—C$R_A$R'—N$R_N$—C(O)$R_C$, a moiety $R_N$ or $R_C$ which represents a protein or polypeptide may be linked to further residues of the other components, if said moiety $R_N$ or $R_C$ includes multiple occurrences of the indicated functional group (e.g., a polypeptide $R_N$—$NH_2$ bearing multiple amino groups, or a polypeptide $R_C$—C(O)OH bearing multiple carboxylic acid groups), as discussed above. In one embodiment, said moieties are not linked to additional residues of the remaining components; that is, the conjugate includes exactly one of each residue $R_I$, $R_A$, $R_N$, and $R_C$. The presence of absence of such additional residues can be controlled by reaction conditions; e.g. by the molar ratios of components present.

The invention includes conjugates having various combinations of the above-referenced components, within the stipulations given above. Typically, the conjugate includes a single protein or polypeptide molecule conjugated to one or two PAO molecules, preferably PEG molecules. Such combinations include conjugates in which:

$R_C$ is a protein, $R_I$ is PEG, and $R_A$ and $R_N$ are independently selected from labeling moieties, targeting moieties, and R;

$R_C$ is a protein, $R_N$ is PEG, and $R_A$ and $R_I$ are independently selected from labeling moieties, targeting moieties, and R;

$R_C$ is a protein, $R_A$ is PEG, and $R_I$ and $R_N$ are independently selected from labeling moieties, targeting moieties, and R;

$R_C$ is a protein, each of $R_N$ and $R_A$ is PEG, and $R_I$ is a labeling moiety, a targeting moiety, or R;

$R_C$ is a protein, each of $R_N$ and $R_I$ is PEG, and $R_A$ is a labeling moiety, a targeting moiety, or R;

$R_A$ is a protein, $R_N$ is PEG, and $R_C$ and $R_I$ are independently selected from labeling moieties, targeting moieties, and R;

$R_A$ is a protein, $R_N$ is PEG, $R_I$ is PEG, and $R_C$ is a labeling moiety, a targeting moiety, or R;

$R_A$ is a protein, $R_C$ is PEG, and $R_I$ and $R_N$ are independently selected from labeling moieties, targeting moieties, and R;

$R_N$ is a protein, $R_I$ is PEG, and $R_A$ and $R_C$ are independently selected from labeling moieties, targeting moieties, and R;

$R_N$ is a protein, $R_A$ is PEG, $R_I$ is PEG, and $R_C$ is a labeling moiety, a targeting moiety, or R;

$R_N$ is a protein, $R_C$ is PEG, and $R_I$ and $R_C$ are independently selected from labeling moieties, targeting moieties, and R; or $R_N$ is a protein, $R_C$ is PEG, $R_I$ is PEG, and $R_A$ is a labeling moiety, a targeting moiety, or R.

In selected embodiments of the above combinations, the non-protein, non-PAO components are embodiments of R. In other embodiments, one such non-protein, non-PAO component is a labeling or targeting moiety.

These and other objects and features of the invention will become more fully apparent when the following detailed description of the invention is read in conjunction with the accompanying drawing(s).

DETAILED DESCRIPTION OF THE INVENTION

I. Definitions

Figure 1:
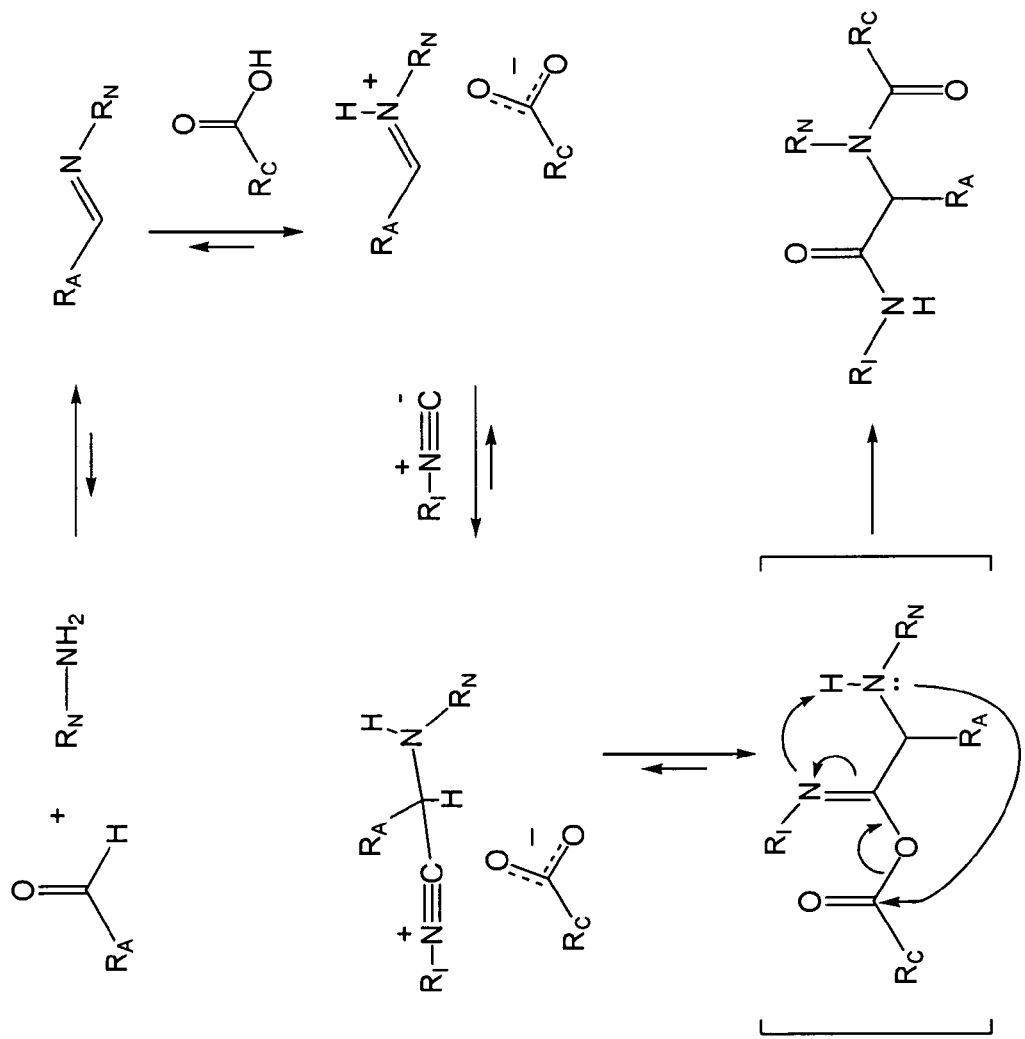
FIG. 1 shows the generally accepted mechanism for a four-component condensation reaction, of which specific embodiments are described herein.

A "polypeptide", as used herein, is a polymer of amino acids, without limitation as to a specific length. Thus, for example, the terms peptide, oligopeptide, protein, and enzyme are included within the definition of polypeptide. This term also includes post-expression modifications of the polypeptide, for example, glycosylations, acetylations, phosphorylations, and the like.

The term "polymer" as used herein is intended to refer to a hydrophilic, preferably water soluble polymer, such as PEG, which is conjugated to a biologically active molecule, even though the latter may itself be polymeric.

"PEG" refers to polyethylene glycol, a polymer having the repeating unit $(CH_2CH_2O)_n$, where n is preferably about 10 to about 2300, which corresponds to molecular weights of about 440 Daltons to about 100,000 Daltons. The polymers are water soluble over substantially the entire molecular weight range. For conjugation to a polypeptide, a preferred range of PEG molecular weight is from about 2,000 to about 50,000 Daltons, more preferably from about 2,000 to about 40,000 Daltons. The PEG may be end capped with any group that does not interfere with the conjugation reactions described herein, e.g. hydroxyl, ester, amide, thioether, alkoxy, or a variety of reactive groups blocked with appropriate protecting moieties. A common end capped PEG is methoxy PEG (mPEG). While PEG homopolymers are preferred, the term may also include copolymers of PEG with another monomer. This could be, for example, another ether forming monomer, such as propylene glycol.

A "biologically active" molecule refers to a molecule known to have biological activity and/or intended for therapeutic or diagnostic use, particularly one expected to have therapeutic activity. Such a molecule may also be referred to as "biologically relevant".

By "stable" and/or "non-interfering", with respect to reaction components of the conjugation reactions described herein, is meant that a reaction component does not undergo any chemical reaction under the conditions of conjugation, other than playing its intended role in the conjugation reaction, and provides a stable, biologically benign substituent on the resulting conjugate.

By "low molecular weight" as used herein, typically in reference to a non-interfering reaction component, is generally meant about 500 Daltons or less, preferably 350 or less, and more preferably 200 or less.

A "carbonyl" component, as used herein with reference to a component of a four-component condensation reaction, refers to an aldehyde or a ketone. The component may be designated by $R_A$—C(O)R', where R' is H or lower alkyl, preferably H or methyl, and more preferably H (i.e. where the carbonyl component is an aldehyde), and $R_A$ is a residue of a biologically active molecule (e.g. a protein or polypeptide), a water soluble polymer, or stable, non-interfering compound as defined herein.

"Alkyl" refers to a fully saturated acyclic monovalent radical containing carbon and hydrogen, which may be linear or branched. Examples of alkyl groups are methyl, ethyl, n-butyl, t-butyl, n-heptyl, and isopropyl. "Cycloalkyl" refers to a fully saturated cyclic monovalent radical containing carbon and hydrogen, preferably having three to seven, more preferably five or six, ring carbon atoms, which may be further substituted with alkyl. Examples of cycloalkyl groups include cyclopropyl, methyl cyclopropyl, cyclobutyl, cyclopentyl, ethylcyclopentyl, and cyclohexyl.

"Lower alkyl" refers to an alkyl radical of one to six carbon atoms, as exemplified by methyl, ethyl, n-butyl, i-butyl, t-butyl, isoamyl, n-pentyl, and isopentyl. In selected embodiments, a "lower alkyl" group has one to four carbon atoms.

"Acyl" refers to an alkyl group, which may be a lower alkyl group, linked to a carbonyl group, i.e. R—(C=O)—.

"Hydrocarbyl" encompasses groups consisting of carbon and hydrogen; i.e. alkyl, alkenyl, alkynyl, cycloalkyl, cycloalkenyl, and non-heterocyclic aryl.

"Aryl" refers to a substituted or unsubstituted monovalent aromatic radical having a single ring (e.g., phenyl), two condensed rings (e.g., naphthyl) or three condensed rings (e.g. anthracyl or phenanthryl). Monocyclic groups are generally preferred. This term generally includes heteroaryl groups, which are aromatic ring groups having one or more nitrogen, oxygen, or sulfur atoms in the ring, such as furyl, pyrrole, pyridyl, and indole. By "substituted" is meant that one or more ring hydrogens in the aryl group is replaced with a halide such as fluorine, chlorine, or bromine; with a lower alkyl group containing one or two carbon atoms; or with nitro, amino, methylamino, dimethylamino, methoxy, halomethoxy, halomethyl, or haloethyl. Preferred substituents, when present, include fluorine, chlorine, methyl, ethyl, and methoxy.

The term "pharmaceutically acceptable salt" encompasses, for example, carboxylate salts having organic or inorganic counterions, such as alkali or alkaline earth metal cations (e.g. lithium, sodium, potassium, magnesium, barium or calcium); ammonium; or organic cations, for example, dibenzylammonium, benzylammonium, 2-hydroxyethyl ammonium, bis(2-hydroxyethyl) ammonium, phenylethylbenzylammonium, and the like. Other cations include the protonated forms of basic amino acids such as glycine, ornithine, histidine, phenylglycine, lysine, and arginine.

The term also includes salts of basic groups, such as amines, having a counterion derived from an organic or inorganic acid. Such counterions include chloride, sulfate, phosphate, acetate, succinate, citrate, lactate, maleate, fumarate, palmitate, cholate, glutamate, glutarate, tartrate, stearate, salicylate, methanesulfonate, benzenesulfonate, sorbate, picrate, benzoate, cinnamate, and the like.

A "pharmaceutically acceptable carrier" is a carrier suitable for administering the conjugate to a subject, including a human subject, as a pharmaceutical formulation. The carrier is typically an aqueous vehicle, such as aqueous saline, dextrose, glycerol, or ethanol. Inactive ingredients, such as buffers, stabilizers, etc., may be included in the formulation. An "aqueous vehicle" as used herein has water as its primary component but may include solutes as just described. Cosolvents such as alcohols or glycerol may also be present.

Solid formulations, which may also be used, typically include inactive excipients such as mannitol, lactose, starch, magnesium stearate, sodium saccharine, talcum, cellulose or cellulose ethers, glucose, gelatin, sucrose, magnesium carbonate, and the like. The conjugate may also be formulated as a suspension in a lipid or phospholipid, in a liposomal formulation, or in a transdermal or inhalable formulation, according to methods known in the art.

II. Macromolecular Conjugates

In accordance with certain aspects of the invention, macromolecular conjugates, comprising at least one biologically active molecule conjugated to at least one water soluble polymer, and methods for their preparation, are provided.

The conjugates are prepared via a four-component condensation (4CC) scheme employing a carboxylic acid component, an amine component, an isonitrile component, and an aldehyde or ketone component, as illustrated in FIG. 1 (wherein an aldehyde component is depicted). The mechanism of the four-component reaction was first described by Ugi et al. (Ugi et al., 1959), and it was recently reviewed (Domling and Ugi, 2000).

In accordance with the invention, the above-referenced four components are selected such that at least one component, selected from the carboxylic acid component, the amine component, and the reactive carbonyl (e.g. aldehyde) component, is present on a biologically active molecule, or macromolecule, preferably a polypeptide, and at least one, different component, selected from the carboxylic acid component, the amine component, the isonitrile component, and the carbonyl component, is present on a hydrophilic polymer, preferably a polyether, such as PEG. The hydrophilic polymer is preferably soluble in aqueous media and is thus preferably uncrosslinked.

Any remaining components not intended as biologically active molecule(s) or hydrophilic polymer(s) are typically provided as stable, stable, non-interfering, preferably low molecular weight compounds. For example, formic or acetic acid may be used as the carboxylic acid component(s), or tert-butyl or cyclohexyl isonitrile may be used as the isonitrile component. These components may form essentially inert substituents (e.g. methyl or other alkyl groups) on the linkage moiety of the conjugate product.

These remaining components may also supply a labeling or targeting moiety to the conjugate. For example, biotin, coumarin-4-acetic acid, 7-aminocoumarin, Lucifer Yellow CH, folic acid, and chelators, such as DTPA, can potentially be utilized for such purposes.

Preferably, the molecular weights of the remaining components are such that they do not sterically interfere with formation of the conjugate. Preferred molecular weight ranges are less than 500, more preferably less than 350, and most preferably less than 200 Daltons.

The components react to form a conjugate incorporating at least one of each moiety represented by $R_A$, $R_N$, $R_C$, and $R_I$. In one embodiment, as discussed above, the conjugate is of the form:

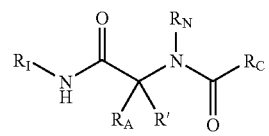

where $R_I$ is derived from the isonitrile component, $R_A$ is derived from the reactive carbonyl (e.g. aldehyde, when R'=H) component, $R_N$ is derived from the amine component, and $R_C$ is derived from the carboxylic acid component. A generally accepted mechanism for the reaction is shown in FIG. 1.

In other embodiments, e.g. in which one of the components (a)-(d) bears more than one of the reactive functionalities indicated (such as a component $R_N$—$NH_2$ bearing multiple amino groups, or a component $R_C$—C(O)OH bearing multiple carboxylic acid groups), the conjugate product may include said component conjugated to multiple residues of the other components. See, for example, the hyaluronic acid conjugate of Example 16, below. The presence, absence, and/or number of such additional residues can be controlled by reaction conditions, such as the molar ratios of components present.

The reaction can be carried out as a "one-pot" reaction. The efficiency of the conjugation may be improved in some cases by first condensing the amine and carbonyl components, thus generating the first intermediate shown in FIG. 1, and subsequently reacting this intermediate with the remaining components (see Examples 7 and 16, below).

A. The Biologically Active Molecule

The biologically active agent is typically a therapeutic or diagnostic agent. Biologically active agents include drug substances selected from polymeric or oligomeric biomolecules, e.g. proteins, polysaccharides, or nucleic acids, or small molecule compounds. A "small molecule" compound may be defined broadly as an organic, inorganic, or organometallic compound which is not a polymer or oligomer. Typically, such compounds have molecular weights of 1000 Da or less, or, in one embodiment, 500 Da or less.

The biologically active molecule is frequently the amine or the carboxylic acid component in the reactions described herein. Such functional groups are commonly occurring in biologically active molecules, e.g. in polypeptides or in various small molecule drug substances.

As discussed above, when the biologically active molecule includes multiple occurrences of an indicated functional group (e.g., a polypeptide $R_N$—$NH_2$ bearing multiple amino groups, or a polypeptide $R_C$—C(O)OH bearing multiple carboxylic acid groups), the residue of the molecule in the conjugate may be linked to additional residues of the remaining components. See, for example, the hyaluronic acid conjugate of Example 16 below. The presence of absence of such additional residues can be controlled by reaction conditions; e.g. by the molar ratios of components present.

When more than one of the different component functional groups is present in the biologically active molecule, reaction conditions are preferably selected to favor the reaction of one over the other. For example, to promote reaction of amine groups over carboxylic acid groups in a molecule, such as a protein, the reaction can be carried out at a high pH (e.g. 7-8.5) and/or in the presence of a high concentration of an acetate buffer, such that the acetate effectively competes with carboxylate groups on the molecule in acting as the carboxyl component of the reaction. Alternatively, to promote reaction of carboxylic acids over amines in a molecule, the reaction can be performed at a low pH. For example, at pH 4-6 the amines in a polypeptide are largely protonated. To further suppress the reactivity of the protein amino groups, the reaction mixture can also include an excess of a low molecular weight, preferably low pKa, amine, such as a hydrazide or an aromatic amine, or an amine-containing buffer, such as TRIS or glycinamide.

In a preferred embodiment, the biologically active molecule, such as a polypeptide or glycopeptide, is the carbonyl, e.g. aldehyde, component in the reaction. While aldehydes occur less commonly in biologically active molecules, e.g. polypeptides, than amines or carboxylic acids, various methods exist for synthetically incorporating a reactive carbonyl into such a molecule. For example, Rodrigues et al. (*J. Org. Chem.* 63:9614, 1998) and Marcaurelle et al. (*Org. Lett.* 3:3691-94, 2001) describe the synthesis of a keto amino acid that can be incorporated into a peptide. Periodate oxidation of 1,2-cis diol or 1,2-aminoalcohol moieties on glycoproteins is a well known method for generating aldehyde groups in these compounds (see e.g. Wilchek, 1987; O'Shannessy, 1987; Morehead, 1991). Galactose oxidase-mediated oxidation of position 6 on galactopyranoside or N-acetyl galactopyranoside residues is another known method of generating reactive aldehydes on a glycoprotein (Wilchek, 1987). Introduction of an aldehyde function on a serine or threonine-containing peptide can be accomplished by DMSO/carbodiimide-mediated oxidation of the hydroxyl groups of these amino acid residues into reactive aldehyde and ketone groups respectively (Di Bello et al. 1972). An aldehyde can also be incorporated into a polypeptide via reaction of an amine on the polypeptide with an appropriate heterobifunctional reagent, e.g. 4-formylbenzoic acid NHS ester, as described by King et al. (1996). Amino groups of peptides or aminosaccharides can be converted into N-levulinoyl residues, for example by the method of Yarema et al. (1998).

Many of the above methods, such as periodate oxidation of glycoproteins (O'Shannessy et al.; Wilchek et al.), provide site-specific generation of reactive carbonyls on polypeptides, thus allowing site selective conjugation of polymers, in accordance with the methods of the invention. Other routes include periodate-mediated oxidation of N-terminal serine- or threonine-containing peptides, which converts them into reactive N-glyoxalyl residues (Dixon, 1987; Geoghegan et al, 1992). N-terminal transamination of peptides is another general method to generate reactive carbonyl group in a site-specific manner (reviewed in Dixon, 1984).

Reactive carbonyls generated in this fashion have previously been used for conjugation of biomolecules with various hydrazide and oxyamine compounds, forming hydrazone and oxime-linked bioconjugates, respectively (Gaerthner et al, 1992; Zalipsky et al, 1995c; Zalipsky and Menon-Rudolph, 1997; Wei et al., U.S. Pat. No. 6,077,939). However, these linkages are labile in acidic pH, particularly in the presence of competing hydroxylamine or hydrazine derivatives. The bioconjugates prepared according to the methods disclosed herein offer much greater stability.

B. The Polymer

The polymer to be conjugated to the biologically active molecule may be any biocompatible polymer which contains or can be modified to contain a reactive group selected from an amine, a carboxylic acid, an aldehyde or ketone, or an isonitrile. Preferably, the polymer is a non-immunogenic hydrophilic polymer. The polymer is preferably water soluble; accordingly, the polymer should be uncrosslinked. Preferably, the polymer is soluble in water at room temperature and physiological pH. Exemplary hydrophilic polymers include polyvinylpyrrolidone, polyvinylmethylether, polymethyloxazoline, polyethyloxazoline, polyhydroxypropyloxazoline, polyhydroxypropyl-methacrylamide, polymethacrylamide, polydimethyl-acrylamide, polyhydroxypropylmethacrylate, polyhydroxyethylacrylate, hydroxymethylcellulose, hydroxyethylcellulose, polyethylene glycol (PEG), polypropylene oxide (PPO), polyaspartamide, and copolymers of the above-recited polymers, e.g. polyethylene oxide-polypropylene oxide copolymers. Properties and reactions of many of these polymers are described in U.S. Pat. Nos. 5,395,619 and 5,631,018. In preferred embodiments, the polymer is a poly(alkylene oxide), such as PPO or PEG, and is more preferably a PEG (polyethylene glycol) polymer. (Note that the terms polyalkylene "oxide" and polyalkylene "glycol" are equivalent.)

Methods for preparation of PEG polymers containing amines, isonitriles, carboxyl groups, or carbonyls are described in Examples 1-4 below; see also Zalipsky (1995b) and Zalipsky & Harris (1997). Other types of hydrophilic polymers, such as those listed above, can be similarly functionalized, using modifications of the procedures of Examples 1-4 for hydroxyl-containing polymers, or according to synthetic procedures available to one skilled in the art.

PEG-isonitrile and PPO-isonitrile derivatives were heretofore unknown. In such derivatives, a preferred range of PEG molecular weight is from about 2,000 to about 50,000 Daltons, more preferably from about 2,000 to about 40,000 Daltons. The PEG may be end capped at the non-isonitrile terminus with any stable end capping group that does not react with the isonitrile or interfere with the conjugation reactions described herein, e.g. ester, amide, thioether, hydroxyl, alkoxy, or a variety of reactive groups blocked with appropriate protecting moieties. A common end-capped PEG is methoxy PEG (mPEG). While PEG homopolymers are preferred, the term may also include copolymers of PEG with another monomer. This could be, for example, another ether forming monomer, such as propylene glycol.

A PAO-isonitrile compound as provided herein typically has the structure $R_{CAP}(OCHR''CH_2)_n-X-N\equiv C$, where $R_{CAP}$ is a stable end capping group; R" is H or methyl, preferably H; X represents a direct bond or a stable linking moiety; and n is an integer between 10 and about 2300, such that the moiety $-(OCH_2CH_2)_n-$ has a molecular weight between about 440 and 100,000 Daltons. In selected embodiments, $R_{CAP}$ is acyl, aryl or alkyl, e.g. methyl.

The linker X, when not a direct bond, preferably consists of linkages selected from linear or branched alkyl, aryl, cycloalkyl, ether, amide, and combinations thereof. More preferably, X consists of linkages selected from lower alkyl, cycloalkyl, aryl and combinations of lower alkyl and aryl or lower alkyl and cycloalkyl. Aryl is preferably monocyclic, e.g. phenyl, and cycloalkyl is preferably cyclopentyl or cyclohexyl. The linker is preferably up to about twelve atoms, more preferably up to about eight atoms, in length. Exemplary linkers include cyclohexyl and lower alkyl, e.g. $-(CH_2)_n-$ where n is 1 to 4.

An exemplary method for preparation of a PEG-isonitrile is provided in Example 1 below. This method employs dehydration of a formamide intermediate, which is in turn prepared by reaction of a PEG amine with ethyl formate. This route could be adapted for the preparation of PEG isonitriles containing stable linkers, such as alkyl or cycloalkyl linkers.

When a polymeric amine component is to be used for conjugation to a polypeptide, it is preferred that the amine functionality on the polymer has a lower pKa than the amino groups on a polypeptide. In this manner, as described below, conjugation with a polypeptide can be carried out at pH 4-7, at which the amino groups on the polypeptide (primarily lysine side chains, which have a pKa of about 10) are protonated and thus unreactive, while the less basic polymeric amine will be unprotonated and thus reactive. A PEG carbazide or hydrazide, having a pKa of about 3, or a PEG conjugated to an aromatic amine, typically having a pKa of about 4, are suitable reagents for this purpose.

In one embodiment of the conjugation reactions described herein, two of the reactive components are provided as functionalized polymeric reagents; for example, a polypeptide or a polysaccharide could be reacted via its carboxyl group with a preformed C=N linked di-PEG adduct formed by a reaction between PEG-amine and PEG-carbonyl components (e.g. entry 4 in Table 1, below; Example 7). Alternatively, PEG-isonitrile and a PEG-carbonyl (e.g. entry 10 in Table 1, below) could be used to achieve single site attachment of two PEG chains. The present reactions can thus provide a polypeptide conjugate having two attached PEG chains linked to one amino acid or sugar residue (entries 4, 5, 7, and 10 of Table 1). Some advantages of multiarmed PEG reagents and their conjugates prepared by alternative chemistry have been previously described (Monfardini et al., 1995; U.S. Pat. No. 5,932,462).

C. Other Reaction Components

In general, a conjugation reaction employs a hydrophilic polymer comprising one of the four required functional groups and a biologically active molecule comprising another of the four required functional groups. It may also be possible to generate a conjugate containing two or even three hydrophilic polymers (or biologically active molecules), by selecting two or three different polymers (or molecules), each comprising a different one of the four required functional groups.

The remaining components (if any; generally one or two) are provided as stable, non-interfering, preferably low molecular weight compounds. By "stable" is meant that the component does not undergo any chemical reaction under the conditions of conjugation, other than playing its intended role in the conjugation reaction, and provides a stable, biologically benign substituent on the resulting conjugate. By "low molecular weight" is meant about 500 Daltons or less, preferably less than 350 Daltons, and more preferably less than 200 Daltons. Examples are compounds having 1-12 carbon atoms and up to about 4 heteroatoms. The nature of $R_N$, $R_C$, $R_A$, and/or $R_I$ (collectively referred to as $R_X$) in these additives is not critical as long as $R_X$ does not adversely interfere with the desired conjugation reaction or the activity or storage stability of the resulting conjugate.

$R_X$ may provide a targeting or labeling moiety. Examples include fluorophores, such as coumarin, fluorescein, and targeting or binding moieties such as biotin, folate, or pyridoxal. Other targeting moieties include those described in co-owned U.S. Pat. No. 6,660,525, which is incorporated herein by reference.

Alternatively, $R_X$ is an inactive, biologically benign, "placeholder" group, which may be represented by R. Preferably, R has 1-12 carbon atoms and may contain up to about 4 heteroatoms. More preferably, R has 1-8 or 1-6 carbon atoms. When R is an embodiment of $R_A$, $R_N$ or $R_C$, R may also be hydrogen. Any functional groups within R should be stable under the conditions of the conjugation reaction. (It is understood that some labeling or targeting moieties could also fall within the definition of R as defined herein.)

R may include aryl groups, as defined above. Preferably, R is non-aromatic and, when not hydrogen or methyl, includes linkages selected from alkyl, alkenyl, ether, hydroxyl, carboxylic ester, and amide. Examples of R include lower alkyl groups, such as methyl, ethyl, isopropyl, or tert-butyl, cycloalkyl groups, such as cyclohexyl, lower hydroxyalkyl groups, lower alkyl esters, lower alkyl ketones, and lower alkyl amides. Compounds which are commonly used as solvents or buffers may be used. Particular examples of such components include TRIS (tris(hydroxymethyl)aminomethane) or glycinamide ($H_2NCH_2C(O)NH_2$) for $R_N$—$NH_2$, acetic acid for $R_C$—COOH, acetaldehyde for $R_A$—CHO, and tert-butyl isonitrile, ethyl isocyanoacetate (C≡NCH$_2$C(O)OEt), or ethyl isocyanopropionate (C≡NCH$_2$CH$_2$CO$_2$Et) for $R_I$—NC. The latter isonitrile is advantageous for characterization of the resulting conjugates, as it incorporates one equivalent of β-alanine into each product conjugate. Standard amino acid analysis can be used to determine the number of thus formed attachments.

Steric considerations should be taken into account when selecting components for the conjugation. Accordingly, if a large molecule and/or polymer is used, or if more than one of either of these entities is to be used, the remaining component(s) are preferably small, low molecular weight compounds, such as lower alkyl derivatives.

II. Reaction Conditions

The reactions are generally performed in polar organic solvents, such as, for example, methanol, trifluoroethanol, or DMF, although there are limited examples in the literature of 4CC reactions being carried out in aqueous media. (de Nouy, 2000; Vredblad, 1973; Goldstein, 1993).

Reaction conditions can be adjusted to produce conjugates having exactly one of each residue represented by $R_A$, $R_C$, $R_I$, and $R_N$, or (when one or more of these components is multifunctional, as discussed above) to have multiple occurrences of selected residues, e.g. by selection of molar ratios of components.

Reaction conditions can also be adjusted to favor reaction of selected functional groups on a component which may contain more than one of the above-referenced functional groups, such as a protein containing both amine and carboxylic acid functional groups. Reaction conditions may be adjusted to suppress reaction of carboxylic acids or amines on a protein, respectively, by including excess low molecular weight carboxylic acid (e.g. an acetate buffer) as the carboxyl component and/or low molecular weight amine (e.g. hydrazine) as the amine component.

Reaction of protein side chain amines can also be suppressed by carrying out the reaction at pH 4-7, at which the side chain amines (primarily lysine side chains, which have a pKa of about 10) are protonated and thus unreactive. In this case, the amine component which is desired to react is preferably a low pKa amine. For example, when a PEG-amine component is to be used for conjugation to a protein (or other biomolecule having reactive amino groups), it is preferred that the PEG-amine functionality has a lower pKa than the amino groups on the protein. In this manner, the PEG amine will be unprotonated, and thus reactive, in a pH range at which the protein side chain amines are protonated. PEG carbazides or hydrazides, having a pKa of about 3, or PEG-aromatic amine reagents, typically having a pKa of about 4, are suitable reagents for this purpose.

In order to increase the efficiency of the conjugation, in some instances, it is advantageous to condense the amine and carbonyl components first, thus generating the first intermediate of the 4CC reaction, and then add to it the remaining components for completion of the conjugation (see Example 7, below).

The conjugation reaction can also be used to generate multiple conjugates simultaneously or in parallel reactions, changing one of the four components or the reaction conditions, thus generating mixtures of various degrees of molecular diversity. The variety of bioconjugates generated in this fashion can be rapidly screened for various chemical and/or biological properties, e.g. molecular weight, polymer content, receptor binding, or cell proliferation. For example, by employing different polymers as one of the components (e.g., various embodiments of $R_I$—NC, where $R_I$ represents different polymers), a plurality of conjugates could be formed having different polymers attached to the same location on a molecule. Alternatively, by employing a particular molecule to represent more than one component (e.g., various embodiments of R—X, where R is a polymer or a molecule to be conjugated, and X represents multiple groups selected from an amine, a carboxylic acid, an aldehyde or ketone, and an isonitrile), a plurality of conjugates could be formed having polymer(s) and/or biologically active molecule(s) attached via different bonds in the conjugate.

III. Exemplary Four-Component Condensation (4CC) Conjugation Scenarios

The table below presents non-limiting examples of various conjugation scenarios, employing, for the purpose of illustration, a protein and a PEG molecule to be conjugated.

In scenarios 1-5, carboxyl groups of proteins are PEGylated, since the protein is the carboxyl component, and at least one of the other components is a PEG reagent. In scenarios 4 and 5, two PEG chains are attached per protein.

In each of scenarios 1-8, where the amine component is not the protein, measures may be taken, as described above, to favor reaction of the desired amine component, $R_N$, over the protein side chains, e.g. by working at low pH (4-6). Furthermore, when PEG is the amine component (as in scenarios 2 and 4-7), a low pKa amine, such as PEG-hydrazide, PEG-carbazide, PEG-oxyamine, or PEG-aromatic amine, can be used. When PEG is not the amine component (i.e. scenarios 1, 3, and 8), an excess of low molecular weight amine, such as TRIS ($H_2NC(CH_2OH)_3$) can be used; a low pKa amine (e.g. glycinamide, acetylhydrazide) may also be provided in excess.

Figure 2:
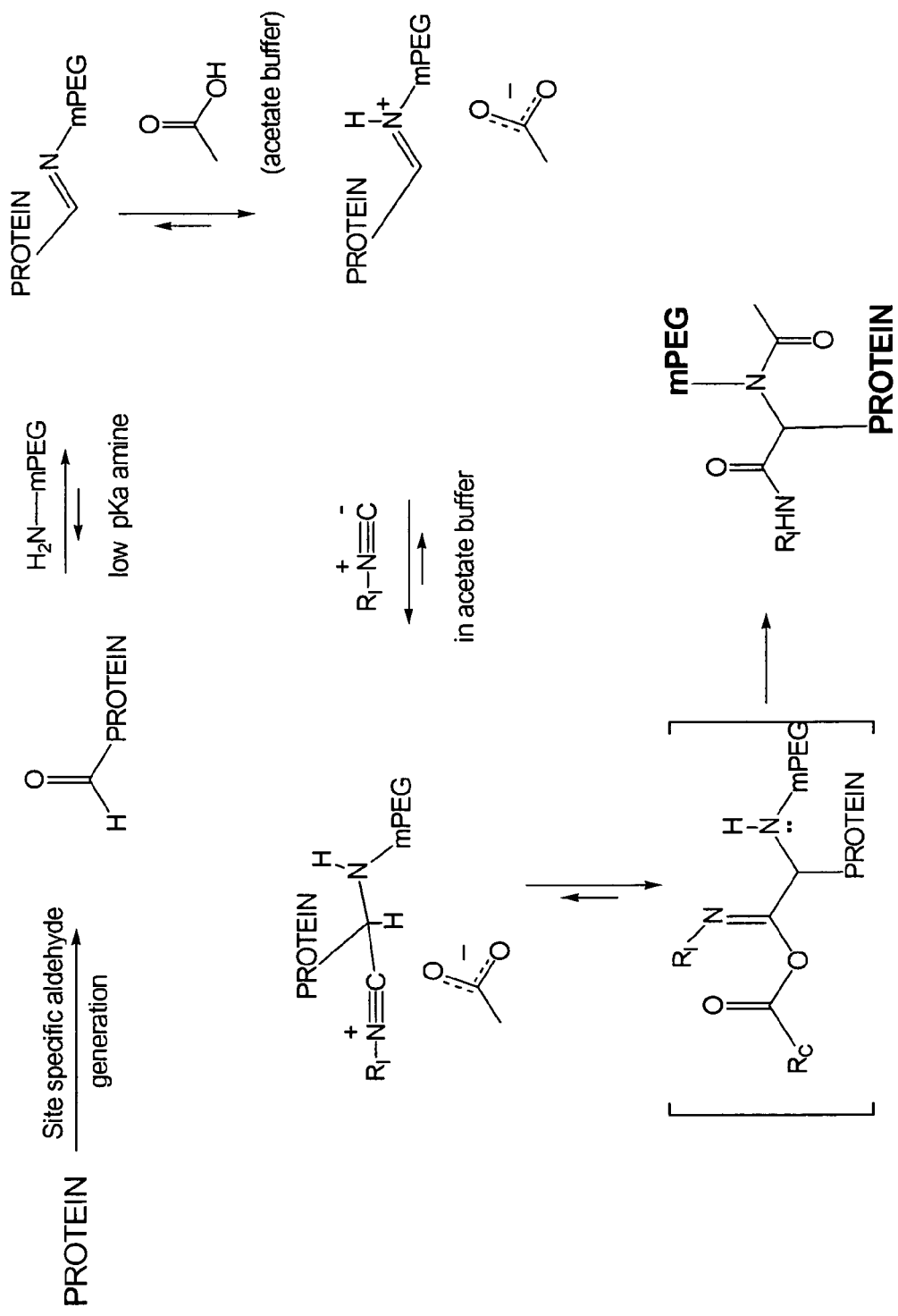
FIG. 2 shows a conjugation scheme illustrating attachment of PEG to a site-specifically generated carbonyl group on a polypeptide, performed in acetate buffer (i.e. $R_C$=CH$_3$), in accordance with one embodiment of the invention. $R_I$ in this case could be, for example, another PAO chain, a label or a small benign residue.

In scenarios 6-8, a synthetically introduced carbonyl group on a protein or glycoprotein is PEGylated. Such a scenario is illustrated in FIG. 2. In the scheme shown in FIG. 2, $R_I$ could represent a small benign residue, a labeling moiety or another PEG chain. As described above, such reactions are particularly attractive because they can provide increased site specificity of attachment (FIG. 2), in comparison to random PEGylation of multiple amino or carboxyl groups on the protein.

In scenarios 9-12, amino groups of proteins are PEGylated, since the protein is the amino component, and at least one of the other components is a PEG reagent. In scenarios 10 and 12, two PEG chains are attached per protein, via amino and carboxyl groups. In reactions 9 and 10, where only amino groups on the protein are to be reacted, an excess of low molecular weight carboxyl component, such as acetic acid as shown, may be used to suppress reaction of carboxyl groups on the protein.

In one embodiment, the isonitrile component is ethyl isocyanopropionate (C≡$NCH_2CH_2C(O)OEt$), as shown. As can be appreciated from the mechanism shown in FIG. 1, this component is converted in the conjugate to a β-alanine moiety (—$NHCH_2CH_2CO_2Et$), which can be detected through amino acid analysis of the conjugated protein product. Such

TABLE 1

Exemplary Conjugation Reaction Scenarios

| Scenario | $R_NNH_2$ (Amine) $R_N =$ | $R_ACHO$ (Carbonyl) $R_A =$ | $R_INC$ (Isonitrile) $R_I =$ | $R_CCOOH$ (Carboxyl) $R_C =$ |
|---|---|---|---|---|
| 1 | —$CH_3$, —$C(CH_2OH)_3$ or —$CH_2CONH_2$ | H, $CH_3$ or other lower alkyl | PEG | Protein |
| 2 | PEG | $CH_3$ or other lower alkyl | t-butyl, c-hexyl, —$(CH_2)_{1-2}CO_2Et$ | Protein |
| 3 | —$C(CH_2OH)_3$ or —$CH_2CONH_2$ | PEG | t-butyl, c-hexyl, —$(CH_2)_{1-2}CO_2Et$ | Protein |
| 4 | PEG | PEG | t-butyl, c-hexyl, —$(CH_2)_{1-2}CO_2Et$ | Protein |
| 5 | PEG | H, $CH_3$ or other lower alkyl | PEG | Protein |
| 6 | PEG | Protein | t-butyl, c-hexyl, —$(CH_2)_{1-2}CO_2Et$ | $CH_3$ |
| 7 | PEG | Protein | PEG | $CH_3$ |
| 8 | —$C(CH_2OH)_3$ or —$CH_2CONH_2$ | Protein | t-butyl, c-hexyl, —$(CH_2)_{1-2}CO_2Et$ | PEG |
| 9 | Protein | H, $CH_3$ or other lower alkyl | PEG | $CH_3$ |
| 10 | Protein | PEG | PEG | $CH_3$ |
| 11 | Protein | H, $CH_3$ or other lower alkyl | t-butyl, c-hexyl, —$(CH_2)_{1-2}CO_2Et$ | PEG |
| 12 | Protein | H, $CH_3$ or other lower alkyl | PEG | PEG | analysis provides a convenient means of determining the conjugate's composition and/or probing the completeness of formation of the conjugation products (see Examples 5, 7, 10, and 11).

EXAMPLES

The following examples are intended to illustrate but not to limit the invention.

Examples 1-4 illustrate exemplary procedures for preparing each component of the conjugation reaction as a hydrophilic polymer, exemplified in these Examples by PEG.

Examples 5-16 illustrate exemplary conjugation protocols, such as those outlined in Table 1 above. Each of these is a one-pot procedure providing a conjugate of a biomolecule with a hydrophilic polymer, exemplified in these Examples by PEG. Example 16 illustrates a conjugate incorporating multiple residues of certain components.

The biomolecules in the Examples include a synthetic adhesion peptide derived from laminin, bovine serum albumin (BSA), erythropoietin (EPO), and hyaluronic acid (HA), a glycosaminoglycan which is used for treatment of connective tissue disorders.

Example 1

Preparation of PEG-Isocyanide (Isonitrile) Derivatives

The general procedure for conversion of mPEG-OH into mPEG-isonitrile, described below for mPEG of molecular weight 2000 Da (mPEG$_{2K}$), is equally applicable to other molecular weight PEGs.

A. Preparation of mPEG$_{2K}$ -NH$_3^+$CH$_3$SO$_3^-$ (mPEG Ammonium Mesylate)

mPEG$_{2K}$ mesylate (Harris et al., *J Polym. Sci. Polym. Chem. Ed.* 22:341 (1984)) (20 g, 9.62 mmol) was dissolved in aqueous ammonium hydroxide (200 ml) in a plastic bottle and stirred at 60° C. for 48 h. The solution was cooled to room temperature, and ammonia was removed from the mixture by evaporation. The residue was lyophilized for 24 h and recrystallized using isopropanol. The product obtained was dried under vacuum over P$_2$O$_5$. The yield of ammonium salt was 91% (18.43 g). $^1$H- NMR (DMSO-d$^6$): 2.30 (s, 3H), 2.97 (t, 2H), 3.23 (s, 3H), 3.50 (bs, 180), 7.63 (bs, 3H).

B. Preparation mPEG$_{2K}$-NH—CHO (MPEG formamide)

mPEG$_{2K}$ ammonium mesylate, prepared as described above (0.5 g, 0.238 mmol), was dissolved in ethyl formate (10 ml) at 60° C. To this solution was added triethyl amine (0.133 ml, 0.954 mmol) and the reaction mixture was heated at 60° C. for 24 h, after which time TLC showed completion of the reaction. Excess ethyl formate was removed by evaporation, and the residue was purified by isopropanol precipitation. The product was dried under vacuum over P$_2$O$_5$. The yield was 88% (0.425 g). $^1$H-NMR (DMSO-d$^6$): 3.19-3.25 (m, 5H), 3.5-3.53 (m, 176H), 3.68 (t, 2H), 8.0 (s, 1H), 8.03 (bs, 1H, exchangeable with D$_2$O).

C. Preparation of mPEG$_{2K}$-NC (mPEG Isonitrile)

mPEG$_{2K}$-formamide, prepared as described above (0.2 g, 0.1 mmol), was dissolved in dichloromethane (2 ml) and cooled to 0° C. To this solution was added carbon tetrachloride (38 µL, 0.3944 mmol) and triethylamine (137 µL, 0.986 mmol), and the solution was stirred at 0° C. for 5 minutes under nitrogen. Tributyl phosphine (98.26 µL, 0.3944 mmol) was then added at 0° C. The reaction mixture was stirred at room temperature for 24 h, during which time it became dark brown. The solvent was evaporated and the product purified by isopropanol precipitation. The yield was 88% (0.175 g). IR (neat): 2150 (NC), $^1$H-NMR (DMSO-d$^6$): 3.23 (s, 3H), 3.41-3.59 (m, 178H), 3.68 (m, 2H).

To prepare mPEG-cyclohexyl isocyanide, MPEG-OH was first activated with carbonyldiimidazole, and then reacted with an excess of 1,4-diaminocyclohexane, following the literature procedure of E. Ranucci and P. Ferrutti (*Synth. Commun.* 20: 2951 (1990)). The resulting mPEG-cyclohexyl amine was converted to the isocyanide in a manner similar to that described above for mPEG-ammonium mesylate.

Example 2

Preparation of PEG-Aldehyde Derivatives

Derivatives of mPEG-acetaldehyde were prepared by literature procedures (e.g. Llanos and Sefton, *Macromolecules* 24:6065 (1991); S. M. Chamow et al., *Bioconjugate Chem.* 5:133 (1994)).

The aromatic aldehyde mPEG-NHC(O)—C$_6$H$_4$—CHO was prepared by reaction of mPEG-amine with 4-carboxybenzaldehyde.

PEG-propionaldehyde derivatives were purchased from Nektar Therapeutics, NOF Corporation, or SunBio Corporation.

Example 3

Preparation of PEG-Amino Derivatives

PEG-amino derivatives were prepared following various literature protocols (reviewed in S. Zalipsky (1995b)). For example, PEG-hydrazide was prepared as described in Zalipsky et al., WO 92/16555 (1992). PEG-carbazide was prepared as described in Zalipsky & Menon-Rudolph (1997). Glycine ester derivatives were prepared as described in Zalipsky et al., *J. Macromol. Sci. Chem.* A21:839 (1984). Aromatic amine derivatives were prepared as described in D. Rozzell, *Meth. Enzymol.* 136:479 (1987); A. Pollak and G. M. Whitesides, *J. Amer. Chem. Soc.* 98:289 (1976); or M. Weber and R. Staddler, *Polymer* 29:1064 (1988).

Example 4

Preparation of PEG-Carboxyl Derivatives

PEG-carboxyl derivatives were prepared according to literature protocols, as reviewed in S. Zalipsky (1995b), or obtained from commercial sources (Nektar Therapeutics, NOF Corporation, or SunBio Corporation).

Example 5

Preparation of PEG-BSA Utilizing R$_N$=mPEG$_{5K}$, R$_A$=CH$_3$, R$_I$=CH$_2$CH$_2$CO$_2$Et, and R$_C$=BSA. (See Scenario 2, Table 1)

In this reaction, PEG is conjugated to bovine serum albumin (BSA), which is employed as the carboxyl component. A low pKa amine component (mPEG$_{20K}$-carbazide) is employed, at pH 5, to favor its reaction over reaction over amino side chains in the protein.

A solution of bovine serum albumin (1 mg/ml, 2 ml) in MES buffer (25 mM) adjusted to pH 5 is treated with ≈20 fold molar excess of mPEG$_{5K}$-carbazide (235 mg), acetaldehyde (1M in acetonitrile, 50 µl), and finally ethyl isocyanopropionate (1M in acetonitrile, 50 µl). The resulting solution is stirred overnight, then dialysed, and further purified by ion exchange chromatography. The product is characterized by SDS-PAGE, MS, and amino acid analysis.

Example 6

Preparation of PEG-Grafted Hyaluronic Acid (HA) Utilizing $R_N$=mPEG$_{5K}$, $R_A$=CH$_3$, $R_I$=CH$_2$CO$_2$Et, and $R_C$=HA. (Analogous to Scenario 4, Table 1)

In this reaction, PEG is conjugated to hyaluronic acid (HA), a carboxylated polysaccharide, which is employed as the carboxyl component.

Sodium hyaluronate (Genzyme, Cambridge, Mass., 6 mg, 15 µmol of carboxyl) is dissolved in water (1.5 ml) and acidified with HCl to pH 4.5. To this solution is added mPEG$_{5K}$-carbazide (25 mg, 5 µmol), followed by acetonitrile solutions of acetaldehyde and ethyl isocyanoacetate (0.1 M, 50 µl, 5 µmol each). The reaction mixture is stirred overnight and then extensively diafiltered (MWCO 100 kDa) against distilled water. PEG content is determined by $^1$H-NMR integration of the acetamido and oxyethylene signals of HA and PEG, respectively, at 2.0 and 3.7 ppm.

Example 7

Preparation of PEG-BSA Utilizing $R_N$=mPEG$_{5K}$, $R_A$=mPEG$_{5K}$, $R_I$=CH$_2$CH$_2$CO$_2$Et, and $R_C$=BSA. (See Scenario 4, Table 1).

In this reaction, two molecules of PEG are conjugated to bovine serum albumin (BSA), which is employed as the carboxyl component. A low pKa amine component (mPEG$_{20K}$-carbazide) is employed, at pH 5, to favor its reaction over reaction over amino side chains in the protein.

Two derivatives of mPEG$_{5K}$, bearing carbazide and aldehyde end groups, respectively (250 mg=50 µmol each), are condensed in acetonitrile solution (2 ml) to form a (mPEG)$_2$-carbazone, the first intermediate in the four component condensation reaction. The solvent is removed by evaporation, and a solution of bovine serum albumin (BSA, 1 mg/ml, 2 ml) in MES buffer (25 mM) adjusted to pH 5 is added, followed by ethyl isocyanopropionate (1M in acetonitrile, 50 µl). The reaction solution is stirred overnight, and the product is dialysed and then further purified by ion exchange chromatography. The product is characterized by SDS-PAGE, MS and amino acid analysis.

Example 8

Preparation of PEG-BSA Utilizing $R_N$=mPEG$_{5K}$, $R_A$=CH$_3$, $R_I$=mPEG$_{5K}$, and $R_C$=BSA. (Analogous to Scenario 5, Table 1).

In this reaction, two molecules of PEG are conjugated to bovine serum albumin (BSA), which is employed as the carboxyl component. A low pKa amine component (mPEG$_{20K}$-carbazide) is employed, at pH 5, to favor its reaction over reaction over amino side chains in the protein.

A solution of bovine serum albumin (1 mg/ml, 2 ml) in MES buffer (25 mM) adjusted to pH 5 is treated with ≈20 fold molar excess of mPEG$_{5K}$-carbazide (235 mg), acetaldehyde (1 M sol. in acetonitrile, 50 µl), and finally mPEG$_{5K}$-NC (250 mg). The resulting solution is stirred overnight, then dialysed, and further purified by ion exchange chromatography. The product is characterized by SDS-PAGE and MS.

Example 9

Preparation of PEG-Grafted Hyaluronic Acid (HA) Utilizing $R_N$=mPEG$_{5K}$, $R_A$=CH$_3$, $R_I$=mPEG$_{5K}$, and $R_C$=HA. (See Scenario 5. Table 1).

In this reaction, two molecules of PEG are conjugated to hyaluronic acid (HA), a carboxylated polysaccharide, which is employed as the carboxyl component.

HA sodium salt (6 mg, 15 µmol of carboxyl) is dissolved in water (1.5 ml) and acidified with HCl to pH 4.5. To this solution is added mPEG$_{5K}$-carbazide (25 mg, 5 µmol), followed by AN acetonitrile solution of acetaldehyde (0.1 M, 50 µl, 5 µmol), and finally by mPEG$_{5K}$-isonitrile (30 mg). The reaction mixture is stirred overnight and then dialysed against distilled water. PEG content is determined by $^1$H-NMR integration of the acetamido and oxyethylene signals of HA and PEG, respectively, at 2.0 and 3.7 ppm.

Example 10

Preparation of mPEG-YIGSR-NH$_2$ Conjugate Utilizing $R_N$=mPEG$_{20K}$, $R_A$=YIGSR-NH$_2$(SEQ ID NO: 1), $R_I$=CH$_2$CH$_2$CO$_2$Et, and $R_C$=CH$_3$. (See Scenario 6, Table 1).

In this reaction, mPEG is conjugated to YIGSR (SEQ IN NO: 1) (a synthetic adhesion peptide derived from laminin) which has been derivatized with an aldehyde group at its N-terminus.

The peptide TYIGSR-NH$_2$ (SEQ ID NO: 2) (5 mM, 0.450 ml) in phosphate buffer (10 mM, pH 7) is treated with a fresh solution of sodium periodate in water (100 mM, 50 µl) for 5 min at 4° C. in the dark, and quenched with sodium sulfite (200 mM, 50 µl). The resulting solution is mixed with mPEG$_{20K}$-carbazide (0.45 g, 22 µmol) solution in acetate buffer (0.5 M, 1 ml, pH 4.5). Ethyl isocyanopropionate (C≡NCH$_2$CH$_2$CO$_2$Et) in acetonitrile (250 mM, 0.1 ml, 25 µmol) is added, and the resulting solution is incubated overnight at room temperature. The product is purified by dialysis followed by ion-exchange chromatography and characterized by MS. N-terminal conjugation is confirmed by sequencing and amino acid analysis.

Example 11

Preparation of PEG-EPO Utilizing $R_N$=mPEG$_{20K}$, $R_A$=gylcan of EPO, $R_I$=CH$_2$CH$_2$CO$_2$Et, and $R_C$=CH$_3$. (See Scenario 6, Table 1)

In this reaction, mPEG is conjugated to EPO (erythropoietin) which has been treated with periodate to produce carbonyl functional groups in the glycan portion of the molecule. A low pKa amine component (mPEG$_{20K}$-carbazide) is used to favor its reaction over reaction over amino side chains in the protein.

A solution of erythropoietin (EPREX®, 0.76 ml, 1 mg) in sodium acetate buffer (0.2 M, pH 5.0) is treated with sodium periodate (80 mM, 40 µl) for 10 min at 4° C. in the dark. The excess periodate is quenched with sodium sulfite (300 mM, 20 µl). mPEG$_{20K}$-carbazide (20 mg, 1 µmol) is added, followed by ethyl isocyanopropionate (20 mM, 50 µl, 1 µmol) in acetonitrile. The resulting conjugation mixture is incubated for 24 h at room temperature. The conjugate is purified by ion-exchange chromatography and characterized by MS, amino acid analysis, and SDS-PAGE. Glycan-specific conjugation is confirmed by determination of the oligosaccharide content.

Example 12

Preparation of mPEG-YIGSR-NH$_2$ Conjugate Utilizing $R_N$=mPEG$_{5K}$, $R_A$=YIGSR-NH$_2$(SEQ ID NO: 1), $R_I$=mPEG$_{5K}$, and $R_C$=CH$_3$. (See Scenario 7, Table 1).

In this reaction, two molecules of mPEG are conjugated to YIGSR (SEQ ID NO: 1) (a synthetic adhesive peptide derived from laminin) which has been derivatized with an aldehyde group at its N-terminus.

The peptide TYIGSR-NH$_2$ (SEQ ID NO: 2) (5 mM, 0.450 ml) in phosphate buffer (10 mM, pH 7) is treated with a fresh solution of sodium periodate in water (100 mM, 50 µl) for 10 min at 4° C. in the dark, then quenched with sodium sulfite (200 mM, 50 µl). The resulting solution is mixed with mPEG$_{5K}$-carbazide (110 mg, 22 µmol) solution in acetate buffer (0.5 M, 1 ml, pH 4.5). A PEG-isonitrile derivative (mPEG$_{5K}$-NC, 125 mg, 25 µmol), prepared as described in Example 1, is added, and the resulting solution is incubated overnight at room temperature. The product is purified by dialysis followed by ion exchange chromatography and characterized by MS. N-terminal conjugation is confirmed by sequencing and amino acid analysis.

Example 13

Preparation of PEG-EPO Utilizing $R_N$=mPEG$_{5K}$, $R_A$=EPO glycan, $R_I$=mPEG$_{5K}$, and $R_C$=CH$_3$. (See Scenario 7, Table 1).

In this reaction, two molecules of mPEG are conjugated to EPO (erythropoietin) which has been treated with periodate to produce aldehyde functional groups in the glycan portion of the molecule. As above, a low pKa amine component (mPEG$_{20K}$-carbazide) is used to favor its reaction over reaction over amino side chains in the protein.

A solution of erythropoietin (EPREX®, 0.76 ml, 1 mg) in sodium acetate buffer (0.2 M, pH 5.0) is treated with sodium periodate (80 mM, 40 µl) for 10 min at 4° C. in the dark. The excess periodate is quenched with sodium sulfite (300 mM, 20 µl). MPEG$_{5K}$-carbazide (100 mg, 1 µmol) is added, followed by mPEG$_{5K}$-isonitrile (100 mg, 1 µmol). The resulting conjugation mixture is incubated for 24 h at room temperature. The conjugate is purified by ion-exchange chromatography and characterized by MS, and SDS-PAGE. Glycan-specific conjugation is confirmed by determination of the oligosaccharide content.

Example 14

Preparation of PEG-BSA Utilizing $R_N$=CH$_3$, $R_A$=H, $R_I$=mPEG$_{5K}$, and $R_C$=BSA. (Analogous to Scenario 1, Table 1).

In this reaction, PEG was conjugated to bovine serum albumin (BSA), which was employed as the carboxyl component. An excess of low molecular weight amine component (methyl amine) was employed, at pH 4.5, to favor its reaction over reaction over amino side chains in the protein.

Specifically, 6 mg of BSA (0.09 µmol) was dissolved in 860 µl of H$_2$O, and the pH was adjusted to 4.5 with 0.25 M HCl (~5 µl). Formaldehyde (9 µmol, 100 fold excess) and methylamine (9 µmol, 100 fold excess) were added, followed by mPEG$_{5K}$N≡C (5 mg, 1 µmol, 11.11 fold excess).

A total of six 25 µl samples were withdrawn, at 5 min., 10 min., 1 h, 4 h, 7.5 h, and 24 h, and each was immediately added to 230 µl of 2M sodium acetate buffer (pH 4.5, ca. 2×10$^5$ fold excess over BSA) to stop the reaction.

The composition of the product at each of these stages was characterized by SDS-PAGE. The amount of PEG-protein conjugate products increased with time, and essentially all the starting BSA was consumed by the 7.5 h time point.

Example 15

Preparation of PEG-Lysozyme Utilizing $R_N$=CH$_3$, $R_A$=H, $R_I$=mPEG$_{5K}$, and $R_C$=Lysozyme. (Analogous to Scenario 1, Table 1).

In this reaction, PEG was conjugated to lysozyme, which was employed as the carboxyl component. An excess of low molecular weight amine component (methyl amine) was employed, at pH 4.5, to favor its reaction over reaction over amino side chains in the protein.

Specifically, 1.4 mg of lysozyme (0.09 µmol) was dissolved in 860 µl of H$_2$O, and the pH was adjusted to 4.5 with 0.25 M HCl (~5 µl). Formaldehyde (9 µmol, 100 fold excess) and methylamine (9 µmol, 100 fold excess) were added, followed by mPEG$_{5K}$N≡C (5 mg, 1 µmol, 11.11 fold excess).

A total of six 25 µl samples were withdrawn, at 5 min., 10 min., 1 h, 4 h, 7.5 h, and 24 h, and each was immediately added to 230 µl of 2M sodium acetate buffer (pH 4.5, ca. 2×10$^5$ fold excess over BSA) to stop the reaction.

Two additional reactions were run, one using 3.1 mg (0.2 µmol) and the other using 7.74 mg (0.5 µmol) lysosome. Quantities of other reagents and reaction conditions were unchanged.

The samples were purified by dialysis with 7000 MWCO Mini dialysis units (Slide-A-Lyzer®, 50 units) against PBS (4 L, pH 7.4) at 4° C. overnight. The composition of the product of each sample was characterized by SDS-PAGE.

The amount of PEG-protein conjugate products increased with time in each reaction, although some protein remained unreacted at 24 hrs, and there was evidence of some formation of protein dimers and trimers.

Example 16

Preparation of PEG-PPO-Hyaluronic Acid Conjugates: $R_N$=PPO, $R_A$=H, $R_I$=mPEG$_{2K}$, and $R_C$=Hyaluronic Acid (Analogous to Scenario 5, Table 1)

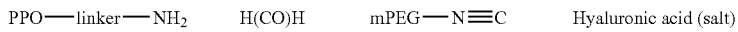

PPO—linker—NH$_2$     H(CO)H     mPEG—N≡C     Hyaluronic acid (salt)

-continued

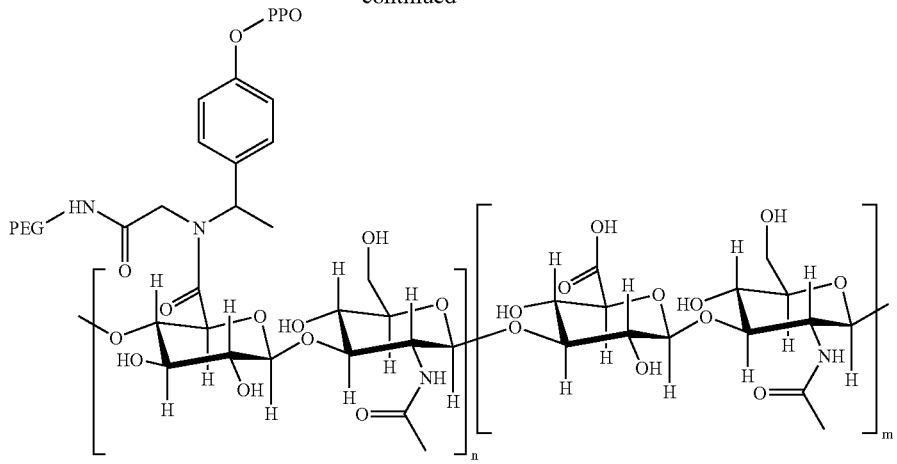

(a) Water (6 ml) was added to sodium hyaluronate (32 mg, 0.08 mmol), and the solution was stirred at room temperature until clear (about 30 minutes). Formaldehyde (6 μl, 0.08 mmol, 37% in $H_2O$) was added to the solution, followed by amino-functionalized polypropylene oxide (PPO—$C_6H_4$—CH($CH_3$)—$NH_2$, 150 mg, 0.08 mmol) in MeOH (12 ml). The resulting solution was slightly acidified with 2N HCl (~36 μl) to obtain a pH of 3-3.5. MPEG isonitrile ($mPEG_{2000}$-NC, 168.08 mg, 0.08 mmol) was added, and the reaction mixture, was stirred at room temperature for 50 h, resulting in a light brown clear solution, which was then lyophilized. The gel-like residue was extracted with $CH_2Cl_2$ to remove unreacted PPO and PEG, and the product was filtered and dried under vacuum over $P_2O_5$. Yield: 36 mg (10%). $^1$H NMR ($D_2O$) δ: 1.02 (br s, $CH_3$ (PPO polymer), 90H), 1.88 (s, $CH_3CONH$ (HA), 3H), 3.4-3.57 (m, PEG+9 HA proton peaks, 189H), 6.95 (d, $C_6H_4$, 2H), 7.3 (d, $C_6H_4$, 2H).

Analysis indicated a conjugate having about 16-17 HA repeating units per PPO/PEG; i.e., m+n in the structure above equals about 16-17. Accordingly, in this conjugate, multiple residues $R_A$, $R_I$ and $R_N$ are conjugated to the residue $R_C$, represented by the hyaluronic acid polymer. (The depiction of the structure above is not meant to imply that the PPO/PEG moieties are necessarily distributed evenly along the HA polymer chain.)

Similar reactions were performed with variations in reaction conditions, as follows.

(b) Repeating the above reaction conditions, but stirring for a shorter time period (24 h), produced a conjugate (28 mg) having about 21-25 HA repeating units per PPO/PEG moiety.

(c) In a further reaction, the original conditions of (a) were followed, with the exception that the pH was adjusted to a higher value (4-4.5). This reaction produced a conjugate (18 mg) having about 10-11 HA repeating units per PPO/PEG moiety.

(d) In a further reaction, the amino-functionalized polypropylene oxide (PPO—$NH_2$) and formaldehyde were first combined and stirred for 2 h, followed by addition of the sodium hyaluronate. The reaction then proceeded as described in the original conditions (a) above. This reaction produced a conjugate (33 mg) having about 11-14 HA repeating units per PPO/PEG moiety.

(e) Finally, the conditions of (d) were followed, with the exception that the pH was adjusted to a higher value (4-4.5). This reaction produced a conjugate (71.6 mg) having about 1-2 HA repeating units per PPO/PEG moiety.

The above results show a trend in which reaction at higher pH produces a higher level of conjugation of PPO/PEG to the HA polymer. Prereaction of the amine and aldehyde components prior to addition of the HA and PEG-isonitrile had a similar but less pronounced effect.

The invention claimed is:

1. A water soluble conjugate of the form $R_I$NH—C(O)—CHR$_A$—NR$_N$—C(O)R$_C$, wherein
   at least one of R$_A$ and R$_C$ is a protein or polypeptide residue;
   at least one of R$_I$, R$_A$, and R$_C$ is a polyalkylene oxide (PAO);
   R$_n$ is —C(CH$_2$OH)$_3$; and
   remaining members of R$_I$, R$_A$, and R$_C$ are independently selected from labeling moieties, targeting moieties, and R, where R is hydrogen or a stable organic moiety having 1-8 carbon atoms and 0-4 heteroatoms selected from oxygen, nitrogen, and sulfur.

2. The conjugate of claim 1, wherein remaining members of R$_I$, R$_A$, and R$_C$ are independently embodiments of R, with the proviso that R$_I$ is not hydrogen.

3. The conjugate of claim 1, wherein R$_I$ is PEG.

4. The conjugate of claim 1, wherein R$_C$ is a protein, R$_I$ is PEG, and R$_A$ is selected from a labeling moiety, a targeting moiety, and R.

5. The conjugate of claim 4, wherein R$_A$ is H or C$_1$-C$_6$ alkyl.

6. The conjugate of claim 5, wherein R$_A$ is methyl.

* * * * *

SEQUENCE LISTING

<160> NUMBER OF SEQ ID NOS: 2

<210> SEQ ID NO 1
<211> LENGTH: 5
<212> TYPE: PRT
<213> ORGANISM: Homo sapiens

<400> SEQUENCE: 1

Tyr Ile Gly Ser Arg
1               5

<210> SEQ ID NO 2
<211> LENGTH: 6
<212> TYPE: PRT

```
<213> ORGANISM: Artificial Sequence
<220> FEATURE:
<223> OTHER INFORMATION: Synthetic adhesion peptide

<400> SEQUENCE: 2

Thr Tyr Ile Gly Ser Arg
1               5
```